(12) United States Patent
Trumm et al.

(10) Patent No.: US 10,716,468 B2
(45) Date of Patent: Jul. 21, 2020

(54) ABERROMETER (OR THE LIKE) HAVING AN ASTIGMATIC TARGET

(71) Applicant: Rodenstock GmbH, Munich (DE)

(72) Inventors: Stephan Trumm, Munich (DE); Gregor Esser, Munich (DE)

(73) Assignee: Rodenstock GmbH, Munich (DE)

(*) Notice: Subject to any disclaimer, the term of this patent is extended or adjusted under 35 U.S.C. 154(b) by 0 days.

(21) Appl. No.: 14/650,354

(22) PCT Filed: Dec. 23, 2013

(86) PCT No.: PCT/EP2013/003939
§ 371 (c)(1),
(2) Date: Jun. 8, 2015

(87) PCT Pub. No.: WO2014/108167
PCT Pub. Date: Jul. 17, 2014

(65) Prior Publication Data
US 2015/0313463 A1    Nov. 5, 2015

(30) Foreign Application Priority Data

Jan. 9, 2013 (DE) .......................... 10 2013 000 295

(51) Int. Cl.
*A61B 3/103* (2006.01)
*G02B 3/06* (2006.01)
(52) U.S. Cl.
CPC ............ *A61B 3/103* (2013.01); *A61B 3/1035* (2013.01); *G02B 3/06* (2013.01)
(58) Field of Classification Search
CPC ........ A61B 3/036; A61B 3/103; A61B 3/1035
(Continued)

(56) References Cited

U.S. PATENT DOCUMENTS

| 4,105,302 A * | 8/1978 | Tate, Jr. ................. A61B 3/028 351/210 |
| 7,341,350 B1 * | 3/2008 | Kadambi ................. A61B 3/09 351/245 |

(Continued)

FOREIGN PATENT DOCUMENTS

| JP | H05-277072 A | 10/1993 |
| JP | H07-067835 A | 3/1995 |

(Continued)

OTHER PUBLICATIONS

Meister, Darryl, and James E Sheedy. Introduction to Ophthalmic Optics. Carl Zeiss Vision, 2008.*

(Continued)

*Primary Examiner* — Zachary W Wilkes
(74) *Attorney, Agent, or Firm* — Schiff Hardin LLP

(57) ABSTRACT

A method and a device for stimulating accommodation of at least one eye of a test person. There is a reliable possibility for determining a set of ophthalmological data relating to at least one eye of the test person and particularly for measuring refractive error of the test person and for determining a corresponding optical correction. The device for determining a set of ophthalmological data relating to at least one eye of a test person, in particular a device for objectively determining refraction comprises: an accommodation stimulating device which is designed to project a virtual target having a spherical effect and having an adjustable cylindrical effect into the at least one eye of the test person; and a measuring device for determining ophthalmological data relating to the at least one eye of the test person.

17 Claims, 3 Drawing Sheets

(58) Field of Classification Search
USPC .................. 351/235, 234, 237, 211, 216, 246
See application file for complete search history.

(56) References Cited

U.S. PATENT DOCUMENTS

| | | | |
|---|---|---|---|
| 7,413,306 B2* | 8/2008 | Campbell | A61B 3/0285 |
| | | | 351/159.68 |
| 9,895,058 B2* | 2/2018 | Baker | A61B 3/103 |
| 2003/0030774 A1 | 2/2003 | Raasch | |
| 2004/0032568 A1 | 2/2004 | Fukuma et al. | |
| 2006/0017864 A1 | 1/2006 | Chae | |
| 2009/0153796 A1* | 6/2009 | Rabner | A61B 3/0091 |
| | | | 351/201 |
| 2012/0287398 A1 | 11/2012 | Baker et al. | |

FOREIGN PATENT DOCUMENTS

| | | |
|---|---|---|
| JP | 2002-010981 A | 1/2002 |
| JP | 2004-089320 A | 3/2004 |
| JP | 2005021181 A | 1/2005 |
| JP | 2006-280614 A | 10/2006 |
| WO | WO-2010/065475 A2 | 6/2010 |

OTHER PUBLICATIONS

International Search Report for PCT/EP2013/003939, EPO, dated May 27, 2014.
Office Action dated Apr. 11, 2017 for Japanese Patent Application No. 2015-551141 (with English translation).
Office Action dated May 15, 2020 for Japanese Patent Application 2019-098834.

\* cited by examiner

ABERROMETER (OR THE LIKE) HAVING AN ASTIGMATIC TARGET

BACKGROUND

The present invention relates to a method and a device for stimulating the accommodation of at least one eye of a subject. In particular, the present invention thereby offers a particularly reliable option for determining a set of ophthalmological data of at least one eye of the subject and, in particular, for measuring the refractive error of the subject and for establishing an appropriate optical correction.

Automated refractors or aberrometers are used ever more frequently for determining a possible refractive error of an eye patient or a customer (referred to as subject below) and for establishing the required optical correction (determining the refraction). By way of example, the prior art includes automated refractors which use simulated eye charts and—analogous to a phoropter—place different powers in front of the subject for subjective refraction and for subjective visual acuity determination. In respect of an automated refractor, reference is made in an exemplary manner to Allergan Humphrey: *Das Humphrey-Refraktometer [The Humphrey refractometer]* (July 2012).

Objective refraction, which is measured by means of a physical arrangement and determined by the refractive properties of the eye (in particular including the cornea, the lens and the vitreous humor), should be distinguished from subjective refraction, which requires information from the subject regarding the perceived image sharpness.

To this end, as is described in "K. Nicke and S. Trumm: *Brillengläser der Zukunft—Schritt 3 Der DNEye Scanner [Spectacle lenses of the future—step three: the DNEye scanner]*, Der Augenoptiker, June 2012", e.g. so-called virtual targets based on optical images are projected into the eye of the subject, by means of which the accommodative states of the eye can be controlled. According to the prior art, this image is realized, in particular, by one or more spherical lenses. A conventional virtual target in this case represents, in particular, an optical imaging system which generates spherical wavefronts emanating from virtual object points such that said wavefronts are incident on the eye of the subject. As a result, the subject has the (virtual) impression of a real object at a specific distance. Ideally, the apparent distance of the depicted object from the eye of the subject is set by the spherical curvature, i.e. the radius of curvature of the wavefronts impinging on the eye. By changing the imaging system of the virtual target, in particular by changing the radius of curvature of the wavefronts impinging on the eye, it is possible to stimulate the eye to accommodate to the different object distances within the physiological possibilities thereof. As a result, the eye can be examined at different accommodative states which, in particular, can be set in a targeted manner and/or the boundaries of the accommodative power of the eye can be gauged.

Conventionally, instruments such as automated refractors and aberrometers perform eye-optical measurements or ophthalmic examinations in the far accommodative state, i.e. in the case of relaxed ciliary muscles. To this end, a virtual target is generated with the aid of at least one spherical lens, which represents an image of an object in the eye of the subject. Here, backlit diapositives are usually used as an object. The position of the at least one lens in relation to the slide and, in the case of a plurality of lenses, also in relation to one another renders it possible in this case to control the image for the limiting case even in such a way that the eye can no longer accommodate to the image (i.e. the virtual object) due to the large virtual object distance, i.e. the image is only identified out of focus in all directions and the aforementioned relaxed state of the eye sets in. This process is also often referred to as "haziness" and the corresponding relaxed state as "hazy state". In order to cause such haziness in a subject, it is necessary to generate an image which is sufficiently beyond the stronger positive principal meridian. This is achieved, independently of the type of refractive error, in a simple manner by the use of lenses with a suitable spherical power.

Eye-optical measurements or ophthalmic examinations for close up, i.e. in the near accommodative state, are comparatively more difficult and less precise. This is firstly due to the fact that although a specific optical distance can be simulated with the aid of a virtual monocular target, other factors influencing the accommodation mechanism of the eye, such as e.g. the binocular disparity (different retinal images of the two eyes) and/or additional information from the scene (location and size of the object relative to other objects in the scene), remain unaccounted for. Secondly, a successful near measurement using a virtual target assumes that the subject also in fact accommodates during the measurement, i.e. that he attempts to see the target in focus.

It is for this reason that the accommodation power in the near-field region (i.e. in the case of a close-up view) which the eye would apply if this were a real target at the corresponding distance often cannot be simulated exactly with the aid of a virtual monocular target as is used in conventional aberrometers and automated refractors. Therefore, an objective refractive measurement only based on a predetermined virtual distance (of the target) for the accommodative state which is present when looking in this distance can be afflicted with significant errors.

SUMMARY

It is therefore an object of the present invention to provide a device and a method which enable a reliable objective refraction measurement by means of an automated refractor, aberrometer or any other eye-optical or ophthalmological measurement instrument, in particular for a close-up view.

This object is achieved by a device and a method according to the independent claims. Preferred embodiments are the subject matter of the dependent claims.

Therefore, in a first aspect, the present invention provides a device for determining a set of ophthalmological data of at least one eye of a subject, in particular a device for objective determination of the refraction, comprising:

an accommodation stimulation apparatus configured to project a virtual target with a spherical power and with an adjustable cylindrical power into the at least one eye of the subject; and a measuring apparatus for registering ophthalmological data of the at least one eye of the subject.

In the context of this description, "ophthalmological data" are understood to mean individual parameters of the at least one eye of the subject. In particular, ophthalmological data comprise sphere and/or astigmatism, but particularly preferably also higher-order aberrations (e.g. coma, spherical aberration, etc.). Moreover, ophthalmological data can alternatively or additionally also comprise pupillometric data, i.e. information in respect of the size (e.g. in the form of a radius), form and/or position (e.g. relative to the corneal vertex or the optical axis of the eye) of a pupil and/or data for describing the wavefront aberration of the at least one eye.

An accommodation stimulation apparatus within the meaning of this invention is an optical system configured to project a virtual object (target) into the at least one eye of the subject in order thereby to stimulate the eye to accommodate to a (virtual) distance set by the virtual target. In other words, a virtual target according to the invention forms an optical imaging system which generates wavefronts emerging from virtual object points such that said wavefronts are incident on the eye of the subject. Here, the wavefronts (in each case corresponding to a virtual object point) generated by the virtual target and incident on the at least one eye of the subject also have an adjustable cylindrical curvature component in addition to a (preferably adjustable) spherical curvature. This cylindrical curvature component is preferably adjustable both in terms of the magnitude of the curvature and also in terms of the axis position. As a result, the cylindrical curvature of the wavefronts then can be set in such a way that it completely or partly corrects an individual astigmatic refraction of the eye of the subject. In the case of complete accommodation of this eye to the virtual object distance (i.e. the spherical curvature of the wavefronts generated by the virtual target), the eye usually consequently perceives the virtual object significantly more in focus than what would be the case without an at least partial compensation of the astigmatic refraction. As a result, the accommodative state of the eye can be stimulated very much more precisely and in a better reproducible manner.

Preferably, the virtual position of the virtual object (target) can be changed such that different accommodative states of the at least one eye can be stimulated in this manner. In particular, the position of the virtual object can preferably be changed between a position for stimulating far accommodation and a position for stimulating near accommodation. Additionally, the position of the virtual object can preferably be set in such a way that the at least one eye of the subject is no longer able to accommodate to the virtual object. In this case, the virtual object (target) can only be perceived out of focus in all directions by the subject. As a result, the ciliary muscles relax. Such a state is referred to as a "hazy" state.

In particular, an optical projection into or onto the eye of the subject is considered a virtual target in such a way that this projection on the retina of the eye generates an image which corresponds to the image of a real object at a specific distance from the eye. For the virtual target, this specific distance is also referred to here as a virtual position. Expressed differently, a virtual target within the meaning of this invention is, in particular, an image of an object in the at least one eye of the subject. By way of example, a backlit diapositive can be used as an object.

Since the virtual target is not (directly) a real object at the virtual position, it is also possible to simulate a virtual position beyond infinity by means of a suitable design of the projection optical system (the accommodation stimulation apparatus). This then corresponds to wavefronts which converge toward the eye (i.e. in the propagation direction).

The virtual target has a preferably adjustable spherical power. Depending on the value of the spherical power of the virtual target, the at least one eye, into which the virtual target is projected, must accommodate more or less strongly so that the subject perceives the virtual target in focus.

It was identified within the scope of the present invention that errors in determining the refraction often occur, particularly for subjects with an astigmatic component in the refractive error. In particular, this is due to the fact that a subject with an astigmatic component in the refractive error does not perceive a virtual target with only spherical power to be completely in focus and equally in focus in all directions. Rather, switching between two accommodative states may occur. Expressed differently, the eye in this case cannot be stimulated to a unique accommodation, leading to errors when establishing ophthalmological data, in particular when determining the (objective) refraction, both in the far accommodation and, in particular, in the near accommodation.

As a result of the virtual target according to the invention which, in addition to the spherical power, also has a cylindrical or astigmatic power which can be adjusted—in particular according to magnitude and direction—it is possible to at least partly lift this problem and significantly increase the reliability and reproducibility of registered ophthalmological data. The virtual target enables a compensation of the astigmatism of the at least one eye of the subject in such a way that the subject can perceive the virtual target in focus in all directions (apart from the higher-order aberrations which are negligible in this context) or at least more in focus than in the case of conventional determinations of the objective refraction. As a result, not only the fixation but, in particular, also the accommodation is made simpler for the subject. Errors when establishing ophthalmological data, in particular when determining the objective refraction, which occur as a result of the subject not correctly or sufficiently affixing the virtual target and/or not correctly or insufficiently accommodating to the target, can thus be reduced or avoided. It is advantageous, even in the far refraction, if the virtual target used for haziness is equally out of focus in all directions on the retina and does not have an astigmatic component induced by the eye (and not compensated for). In particular, the hazy state generated thereby is more pleasant to the subject.

The measuring apparatus for registering ophthalmological data of the at least one eye of the subject preferably comprises an illumination apparatus, in particular a laser or a laser diode, for illuminating a point on the retina of the eye. A spherical wave then emanates from this point and is refracted at the optical interfaces of the eye (vitreous humor, lens surfaces, cornea). The measuring apparatus preferably also has a detector for detecting the wavefront aberration of at least a part of these resulting waves. The ophthalmological data can be established from the detected signal.

The accommodation stimulation apparatus preferably has at least one spherical lens or spherical lens system, i.e. a lens (or a lens system) with a spherical power, and at least one cylindrical lens or cylindrical lens system, i.e. a lens (or a lens system) with a cylindrical power. The lenses are preferably arranged in a movable manner. The position of the at least one spherical lens in relation to the object to be imaged (e.g. diapositive) and, in the case of a plurality of lenses, also in relation to one another in this case renders it possible to set or change the virtual position of the virtual target.

A preferred embodiment of the device according to the invention for determining a set of ophthalmological data relates to the device described above, wherein the accommodation stimulation apparatus comprises a magazine, e.g. a revolver magazine, with a multiplicity of cylindrical lenses, which each have different cylindrical powers. Preferably, the magazine is configured and arranged in such a way that individual cylindrical lenses or a combination of a plurality of cylindrical lenses of the magazine are selectable and employable for projecting the virtual target.

The cylindrical lenses are preferably selected automatically and inserted into the beam path for imaging the object in the at least one eye of the subject in addition to the lenses which are responsible for the spherical power of the virtual target. Expressed differently, the various cylindrical lenses of the magazine can be held selectively in front of the at least one eye of the subject. Here, the cylindrical power is selected by way of the selection of the cylindrical lenses. By way of example, the magazine can contain lenses with a grading of 0.25 dpt or 0.125 dpt. The cylindrical lenses preferably cover a range of the cylindrical power, the magnitude of which covers a range from at least approximately 0 to approximately 2 dpt, preferably from at least approximately 0 to approximately 4 dpt, even more preferably at least from approximately 0 to approximately 6 dpt, in particular at least partly with the aforementioned gradation. Particularly preferably, provision is also made for lenses with a cylindrical power with a magnitude in the region of approximately 8 dpt to approximately 10 dpt or more. Here, it is sufficient to store only positive or only negative powers since every conventional or required spherical equivalent s can be implemented in the case of a suitable selection of the spherical power $s_G$ of the main system (the main system comprises no lenses of the magazine). The cylindrical power c then corresponds to the cylindrical power of the cylindrical lens selected from the magazine $c_M$. The spherical equivalent therefore emerges as:

$$s = s_G + c_M \quad c = c_M.$$

Analogously, different axis positions in combination with the powers can be stored as respective individual lens. Preferably, the selected lens can be accordingly aligned along the optical axis by rotation prior to insertion into the beam path or within the beam path.

The accommodation stimulation apparatus preferably comprises an Alvarez lens system. By way of example, an Alvarez lens is described in H. Paul: *Lexikon der Optik* [*Optics encyclopedia*], Spektrum Akademischer Verlag GmbH (2003). An Alvarez lens system (Alvarez lens) consists of two lens elements which are arranged along a common optical axis (z-direction) and which are displaceable relative to one another. The curved surfaces of the two lens elements can be described by the following equation:

$$z = axy^2 + (a/3)x^3 + bx \tag{2}.$$

Here, x, y and z describe Cartesian coordinates of the lens system, wherein the z-direction defines a common axis of the two lens elements and therefore the optical axis. Furthermore, a and b are constants. As a result of a relative translation movement of the two lens elements perpendicular to the optical axis (i.e. in the x-direction or y-direction), it is possible to change both the spherical power (in the case of a relative movement of the lens elements along the x-direction) and the cylindrical power (in the case of a relative movement of the lens elements along the y-direction which is perpendicular to the x-direction and z-direction) of the Alvarez lens system. Expressed differently, an Alvarez lens system enables a continuous change in the spherocylindrical power. In the case of an exact overlap, the two lens elements neutralize one another to have zero power. In the case of mutual displacement of the lens elements in the x-direction, positive (spherical) optical powers are generated toward one side and negative (spherical) optical powers are generated toward the other side. In the case of the mutual displacement in the y-direction, variable cylindrical powers emerge, and in the case of oblique displacements spherocylindrical combinations emerge as a function of the size and direction of the displacement.

Consequently, an Alvarez lens is advantageous in that it is variably adjustable not only in respect of the cylindrical power but also in respect of the spherical power. If no importance is placed on changing the spherical power, rather this is realized by additional spherical lenses and/or a movement of the Alvarez lens system along the optical axis (z-direction) in relation to the other optical elements of the system, a translation along the direction of the spherical power (x-axis) can be dispensed with. The Alvarez lens can be mounted in a manner rotatable about the optical axis (z-axis) for setting the direction of the cylinder axis.

In a preferred embodiment, the accommodation stimulation apparatus comprises at least two lenses which are rotatable in relation to one another and which respectively have at least one cylindrical component in the powers. Preferably, these lenses are arranged coaxially with respect to one another and rotatable relative to one another about the common optical axis. Preferably, they are rotatably mounted independently of one another about the common coaxial axis in each case and they particularly preferably have the same cylindrical powers in terms of magnitude.

By rotating the two coaxially arranged lenses against one another, it is possible to set the strength of the cylinder (cylindrical power). The axis position can be set by a common rotation of the two lenses. According to "Breitenstein: *Allgemeine Optik* [*General optics*], script for the lecture at HFA Cologne (2004), the combined power ($c_K$, $a_K$) of two lenses with astigmatic power and the cylindrical components $c_1$ and $c_2$ emerges as a function of the axis positions $a_1$ and $a_2$ within the thin-lens approximation and in the case of negligible spacing as follows:

$$c_K = \sqrt{c_1^2 + c_2^2 + 2c_1 c_2 \cos(2(a_1 - a_2))} \tag{3}.$$

In this representation, the plus cylinder notation is used in a simplified manner. That is to say, $c_1$, $c_2 \geq 0$.

Preferably, both lenses have the same magnitude of cylindrical power because ideal cancellation of the cylindrical components is only possible in this way. Furthermore preferably, the magnitude of the cylindrical power for the two lenses is in each case half the magnitude of the maximum cylindrical power to be obtained $$\left(c_1 = c_2 = \frac{c_{Max}}{2}\right)$$

or slightly larger. Thus, the complete range of cylindrical power from zero to a desired maximum value can be implemented. Equation (3) above is therefore simplified to:

$$c_K = \tfrac{1}{2} c_{max} \sqrt{2 + 2\cos(2(a_1 - a_2))} \tag{4}.$$

Preferably, the axis positions $a_1$ and $a_2$ of the two coaxially arranged lenses are given by:

$$a_{1,2} = a_K \pm \frac{1}{4} \cdot \arccos\left(\frac{2c_K^2 - c_{Max}^2}{c_{Max}^2}\right), \tag{5}$$

where $a_K$ is the combined axis position, $c_K$ is the combined cylindrical power and $c_{Max}$ is the maximum magnitude of the cylindrical power to be obtained.

Preferably, the two coaxially arranged lenses are positive cylindrical lenses with the same strength (with the same cylindrical power) or negative cylindrical lenses with the same strength or a positive and a negative cylindrical lens. A cylindrical lens is understood to mean a lens which has no power in the principal meridian that is smaller in terms of magnitude. The strength thereof is defined analogously as the power in the principal meridian that is larger in terms of magnitude.

In a preferred embodiment, the two lenses have mutually engaging rotationally symmetric surfaces, preferably plane surfaces, wherein these surfaces face one another. This embodiment is advantageous in that this allows a small distance to be realized between the lenses.

In a preferred embodiment, the accommodation stimulation apparatus has a positive and a negative cylindrical lens with equal and opposite powers, said cylindrical lenses being rotatably mounted in relation to one another and preferably being displaceable in relation to one another.

Preferably, the accommodation stimulation apparatus has a so-called Stokes lens, by means of which specific astigmatic powers can be set continuously. A Stokes lens is a combination of a positive and a negative cylindrical lens with equal and opposite strength or power. The cylindrical lenses used here each preferably have a plane surface and a positively or negatively curved cylinder surface.

By way of example, a Stokes lens is described in "H. Paul: Lexikon der Optik, Spektrum Akademischer Verlag GmbH (2003). Equation (4) for the strength $c_K$ of the resulting cylinder is simplified to:

$$c_K = c_{Max} \cdot \sin(\Delta a) \quad (6)$$

in the case of a Stokes lens, where $\Delta a$ is the angle between the cylinder axis $a_p$ of the positive cylindrical lens and the cylinder axis $a_n$ of the negative cylindrical lens. Here, in this context, the cylinder axis in the case of cylindrical lenses is understood to be in particular the axis with the power (independently of the sign of the power).

Preferably, at least one lens of the above-described lens systems is displaceable along the optical axis. Particularly preferably, all lenses of the above-described lens systems are displaceable along the optical axis. A possible change in the strength of the spherical power can then be taken into account when calculating the positions relative to other optical components of the accommodation stimulation apparatus, which positions are required for obtaining predetermined spherical powers of the virtual target.

Preferably, the device for determining a set of ophthalmological data is embodied as an aberrometer and/or automated refractor. More preferably, the device additionally comprises a wavefront sensor, for example a Shack-Hartmann sensor, for determining the wavefront of the at least one eye of the subject.

The measuring apparatus is preferably configured to register an astigmatic refraction (i.e. refractive error) of the at least one eye of the subject, in particular measure it as at least part of ophthalmological data. Moreover, the device preferably comprises a control apparatus configured to set, preferably automatically, the cylindrical power of the virtual target in such a way that the registered astigmatic refraction of the at least one eye is at least partly, preferably even at least mainly or substantially completely, compensated thereby. Hence, ophthalmological data for a subject can be determined very reliably and at least largely in an automated and objective manner by virtue of the desired or required cylindrical power of the virtual target preferably being set automatically. In other embodiments, the cylindrical power of the virtual target can also be set by a user (in particular manually), for example on the basis of a value of the astigmatic refraction of the subject which was already established in advance.

The device is particularly preferably configured to successively set different virtual distances of the virtual target and to register ophthalmological data of the at least one eye for each virtual distance. Here, an astigmatic refraction of the at least one eye is registered particularly preferably with each registered data set, i.e. at each set virtual distance (except for possibly in the case of the last measurement step), and the cylindrical power of the virtual target is set in accordance with the registered astigmatic refraction in the respectively successive virtual distance. Expressed differently, the astigmatic refraction registered in a first step (i.e. at a first virtual distance) is consequently used for setting, on the basis thereof, the cylindrical power of the virtual target for an (immediately following) second step (i.e. at a second virtual distance) in such a way that the registered astigmatic refraction is consequently at least partly compensated for in the above-described manner. This is particularly advantageous if the difference between successively set virtual distances is not too large.

Particularly preferably, the device (or a corresponding method for stimulating the accommodation) starts at a large virtual distance, in particular in a "hazy" state and successively reduces the virtual distance (preferably continuously) from measurement to measurement, preferably to a near accommodation limit, at which the accommodation of the eye can no longer follow the further reduction in the virtual distance.

In a further aspect, the invention provides a method for stimulating the accommodation of at least one eye of a subject. The method comprises registering a (first) value of an astigmatic refractive error (astigmatic refraction) of the at least one eye of the subject. To the extent that it is still unclear as to whether the eye to be examined of the subject has an astigmatic refractive error and, if so, what it is, said refractive error is preferably initially measured or estimated. Particularly preferably, the (first) value of the astigmatic refractive error is measured at a far accommodation of the eye and/or in the hazy state, in particular, by means of a device according to the invention (for example in the case of presetting the virtual target with a cylindrical power of zero). To the extent that a measurement of the astigmatic refractive error was already performed in advance and possibly even already used for already available spectacles, it is possible to resort to these known values.

According to the invention, a virtual target with a (first) spherical power and an adjustable (first) cylindrical power is now provided and projected into the at least one eye of the subject in such a way that the (first) cylindrical power of the virtual target at least partly compensates the registered (first) value of the astigmatic refractive error of the at least one eye.

In a preferred embodiment, the method comprises a pre-measurement, which already comprises a step of projecting a virtual target with spherical (and adjustable cylindrical) power into the at least one eye of the subject while the eye is accommodated to the virtual target or a hazy state of the eye is assumed (the eye is consequently unable to completely accommodate). To this end, the method preferably comprises a step of registering or establishing the first value of the astigmatic refractive error of the at least one eye of the subject. Preferably, a (first) value of the spherical refractive error of the at least one eye of the subject is also registered in addition to the astigmatic refractive error. A first value of an astigmatic refractive error and/or a spherical refractive error of the at least one eye of the subject is preferably established in the hazy state. The hazy, i.e. relaxed, state can be realized by virtue of the virtual distance of the virtual target being selected to be sufficiently far from the at least one eye of the subject such that the at least one eye is no longer able to accommodate to the virtual target and the subject can only perceive the virtual target out of focus. Particularly preferably, the pre-measurement is performed in the only slightly hazy state, i.e. at a virtual position of the virtual target at which the at least one eye of the subject is just no longer able to accommodate to the virtual target.

After the step of registering a first value of an astigmatic refractive error of the at least one eye of the subject, more particularly within the scope of a pre-measurement, the method comprises a step of setting the cylindrical power of the virtual target to a value which substantially compensates the registered first value of the astigmatic refractive error of the at least one eye of the subject. Setting the astigmatic power of the virtual target can, for example, be implemented by selecting appropriate lenses from a magazine of the accommodation stimulation apparatus. Alternatively, the astigmatic power of the virtual target can be set by setting the relative position or aligning lenses of a lens system (e.g. Alvarez lens or Stokes lens).

In a preferred aspect, the invention provides a method for determining a set of ophthalmological data of at least one eye of a subject. Here, the accommodation of the at least one eye is initially stimulated in the inventive manner by means of a virtual target with an adjustable cylindrical power. The ophthalmological data of the eye are registered while the eye accommodates to the correspondingly set virtual target.

Therefore, after the step of setting the cylindrical (astigmatic) power of the virtual target to a value which substantially compensates the registered first value of the astigmatic refractive error of the at least one eye of the subject, the method preferably comprises a step of registering ophthalmological data of the at least one eye of the subject within the scope of the main measurement (e.g. second measurement). Compared to a first measurement (pre-measurement), the second measurement (main measurement) serves in particular to determine ophthalmological data more precisely, in particular the refraction of the at least one eye of the subject, and it is therefore also referred to as main measurement here. In order to increase the accuracy of the measured values or in order to reduce possible measurement errors, a multiplicity of main measurements are preferably performed and the results thereof are averaged out statistically.

Preferably, the registration of the ophthalmological data of the at least one eye of the subject is implemented during a near accommodation of the at least one eye of the subject. In particular, the virtual target is brought to a specific or predetermined virtual distance from the at least one eye of the subject for the purposes of registering the ophthalmological data of the at least one eye of the subject. In general, the virtual target can be brought into a virtual position for far accommodation or near accommodation. However, the virtual target can also be brought into a virtual position which brings about a hazy state.

In a preferred embodiment, registering the ophthalmological data comprises a registration of a second value of the astigmatic refractive error of the at least one eye. Particularly preferably, the method in this case furthermore comprises the projection of the virtual target with a second spherical power, which may also correspond to the first spherical power but preferably differs therefrom, and a second cylindrical power into the at least one eye in such a way that the second cylindrical power of the virtual target at least partly compensates the registered second value of the astigmatic refractive error. More preferably, the method in this case comprises a registration of further ophthalmological data of the at least one eye while the eye is stimulated to accommodate to the virtual target with the second cylindrical power. This process can also be repeated a number of times by virtue of the further ophthalmological data in turn comprising an astigmatic refractive error of the eye, to which the cylindrical power of the target is set for an in turn subsequent step of registration of ophthalmological data in the case of a further accommodative state of the eye (due to a further virtual distance of the virtual target).

In particular, the method therefore preferably comprises a step of registering ophthalmological data of the at least one eye of the subject in at least one further (i.e. a third, fourth, fifth, etc.) measurement, which is performed at an optical (virtual) distance, differing from that in the preceding measurements, of the virtual target to the at least one eye of the subject, wherein, prior to performing the at least one further (i.e. third, fourth, fifth, etc.) measurement, the adjustable cylindrical power of the virtual target is preferably set to a value which substantially compensates the value of the astigmatic refractive error of the at least one eye of the subject registered during the respectively preceding (second, third, fourth, etc.) measurement.

Like the second measurement, the at least one further (third, fourth, fifth, etc.) measurement also serves for precisely determining ophthalmological data, in particular for determining the refraction, such that the at least one further (third, fourth, fifth, etc.) measurement could also be referred to as a main measurement. Expressed differently, the cylindrical power of the virtual target is adjusted prior to each main measurement, preferably on the basis of an (in particular immediately) preceding measurement, in such a way that the astigmatic refractive error of the at least one eye of the subject, established by the preceding measurement, is substantially compensated for. The second measurement is preferably performed at a virtual position of the virtual target which brings about a hazy state. The optical distance of the virtual target can then be successively reduced for each further (third, fourth, fifth, etc.) measurement.

In a preferred embodiment, ophthalmological data of the at least one eye of the subject are registered continuously in the second measurement during a monotonic displacement of the virtual target from a position for stimulating a far accommodation via a position for stimulating a near accommodation up to a position for generating a hazy state. Preferably, the second measurement starts at a sufficiently large virtual distance of the virtual target which brings about a hazy state.

Preferably, all measured values for each virtual position of the target are logged during the whole process. It is then possible, at the end of the measurement process, to select the measurement at which the maximum accommodation power of the at least one eye of the subject was reached. The data obtained from this measurement can be used as a result of the near measurement. In this manner, it is possible to realize a complete measurement of wavefront, pupil dimensions and the aberrations of higher and lower order for the close-up view.

In a preferred embodiment, the method comprises (preferably substantially continuous) changing of the spherical power of the virtual target from the first spherical power to a second spherical power while the virtual target with a cylindrical power is projected into the at least one eye of the subject in such a way that the cylindrical power of the virtual target at least partly compensates the registered first value of the astigmatic refractive error of the at least one eye.

Here, it is not necessary for there to be a measurement of ophthalmological data at each value, or even only at a multiplicity of values, of the spherical power. Nor is it mandatory for the cylindrical power to be updated during the change in the spherical power.

In a preferred embodiment, there can be, for example, a change in the spherical power from a state of the far accommodation or a hazy state to a state of the near accommodation, wherein an objective measurement of ophthalmological data then is implemented in the state of the near accommodation. Here, the cylindrical power of the virtual target is maintained in a preferred embodiment. As a result of the at least partial compensation of the astigmatic refractive error during the projection of the virtual target, the eye can be stimulated in a very precise reproducible manner to accommodate in the transition from a relaxed state to a state with near accommodation. As a result, the measurement of the ophthalmological data in the near accommodation is substantially improved.

In a further preferred embodiment, a (continuous) change in the cylindrical power of the virtual target is also brought about during the (continuous) change in the spherical power. Here, the change in the cylindrical power can for example be based on a (quasi-continuous) measurement of the astigmatic refractive error, as already described above, or on a fixed model prescription.

DRAWINGS

Preferred embodiments of the invention are explained in an exemplary manner below with reference to the appended drawings. Here, the individual described embodiments in part have features which are not mandatory for carrying out the claimed subject matter but which, in specific applications, provide desired properties. Thus, embodiments which do not have all of the features of the embodiments described below should also be considered as being disclosed by the described technical teaching. Furthermore, certain features are only mentioned in relation to individual ones of the embodiments described below in order to avoid unnecessary repetition. Reference is made to the fact that the individual embodiments should consequently not only be considered on their own, but also be considered in an overall view. On the basis of this overall view, a person skilled in the art will recognize that individual embodiments can also be modified by including individual features, or a plurality of features, from other embodiments. Reference is made to the fact that a systematic combination of the individual embodiments with individual features, or a plurality of features, which are described in relation to other embodiments can be desirable and expedient and should therefore be taken into consideration and also be considered to be comprised by the description. In particular, the device according to the invention is preferably configured to carry out one of the methods disclosed in this description. In view of the subsequent description of preferred embodiments:

DETAILED DESCRIPTION

Figure 1:
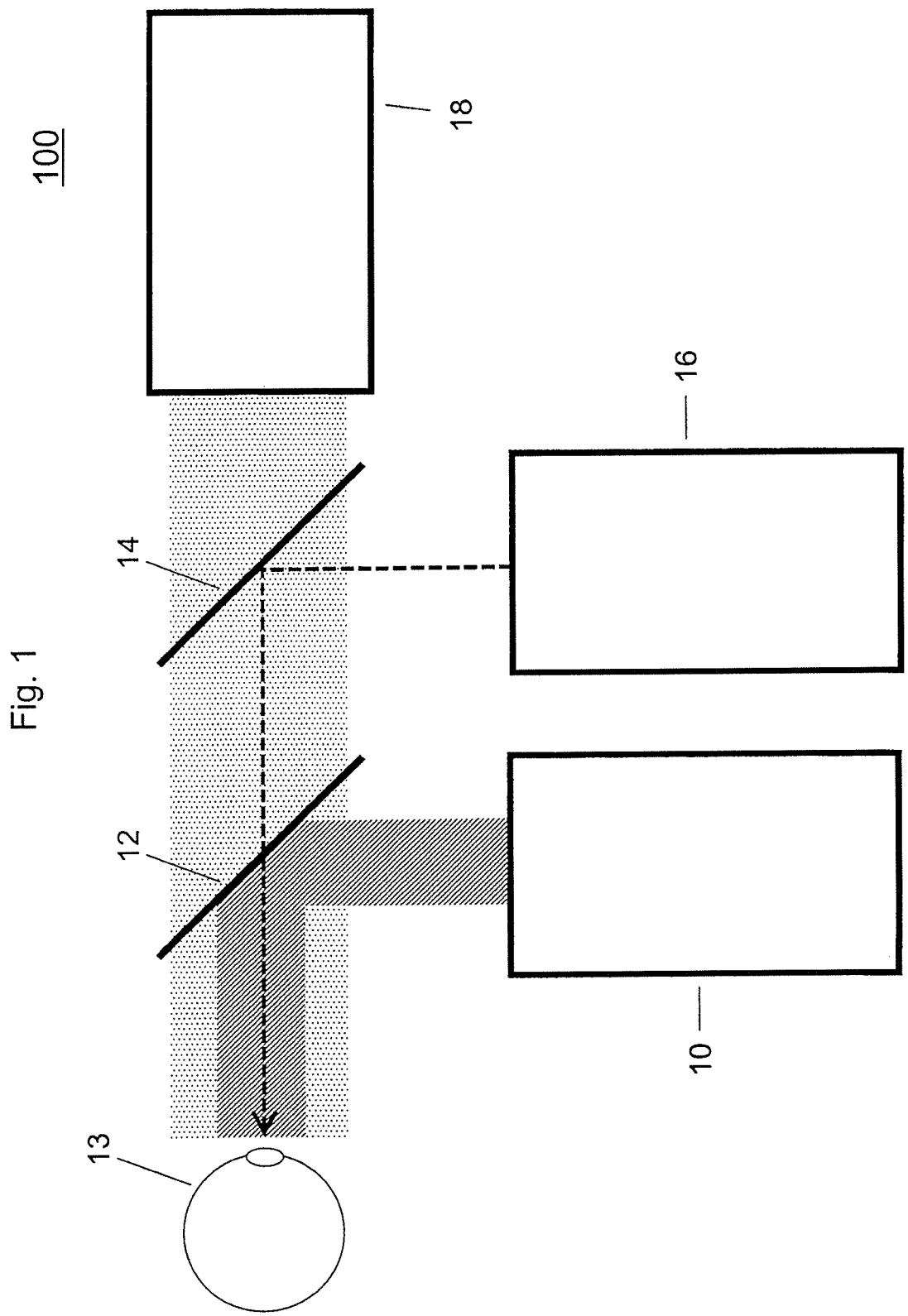
FIG. 1 shows a schematic illustration of a device in accordance with a preferred embodiment of the present invention.

FIG. 1 shows a schematic illustration of a device for determining ophthalmological data of at least one eye of a subject in accordance with a preferred embodiment of the present invention. The device comprises an accommodation stimulation apparatus 10, by means of which a virtual target is generated and, via a first beam splitter 12, projected into the at least one eye 13 of the subject. The virtual target is accordingly an image of an object, preferably of a backlit diapositive, on the retina of the at least one eye 13 of the subject.

With the aid of the virtual target it is possible to stimulate the accommodation of the at least one eye of the subject. The strength of the stimulated accommodation depends on the virtual position of the virtual target or on the virtual distance of the virtual target from the at least one eye 13 of the subject, which can be set by means of the accommodation stimulation apparatus 10.

The accommodation stimulation apparatus 10 preferably substantially comprises the diapositive (slide), an illumination apparatus for providing the diapositive with backlighting and an optical system with at least one spherical lens. The optical system can image the backlit diapositive on the retina of the eye 13 in such a way that the image of the diapositive or the virtual target appears to be at a specific virtual distance from the subject. The position of the at least one spherical lens from the slide and, in the case of a plurality of lenses, also the distance from one another renders it possible to control the virtual position of the virtual target or the virtual distance of the virtual target from the at least one eye 13 of the subject and hence to control the accommodation stimulation of the eye 13.

Thus, for example, the virtual position of the virtual target can be set in such a way that a near accommodation (relatively small virtual distance of the virtual target) or a far accommodation (relatively large virtual distance of the virtual target) is stimulated. Accordingly, it is also possible to set the virtual distance of the virtual target to a sufficiently small or sufficiently large value such that the eye 13 can no longer accommodate to the image, and so the latter is only identified out of focus. Consequently, a relaxed or hazy state for the at least one eye 13 of the subject sets in. Targeted generation of such a state is referred to as "haziness". To this end, it naturally suffices merely to work with spherical powers since these are already sufficient for providing an eye (with a refractive error) with an image which can only be perceived out of focus in all directions, even if an astigmatic component of the refractive error is present in the eye. All that is required is to select an image which is sufficiently beyond the stronger positive principal meridian.

Although it is possible to carry out refraction measurements on the basis of a virtual target by means of lenses which only have a spherical power, the accommodation stimulation apparatus 10 has, in addition to, or in place of, the at least one spherical lens, at least one cylindrical lens, preferably a plurality of cylindrical lenses (e.g. a revolver magazine of cylindrical lenses), or a lens system with an adjustable cylindrical power, which can be placed in front of the at least one eye 13 of the subject.

Figure 2:
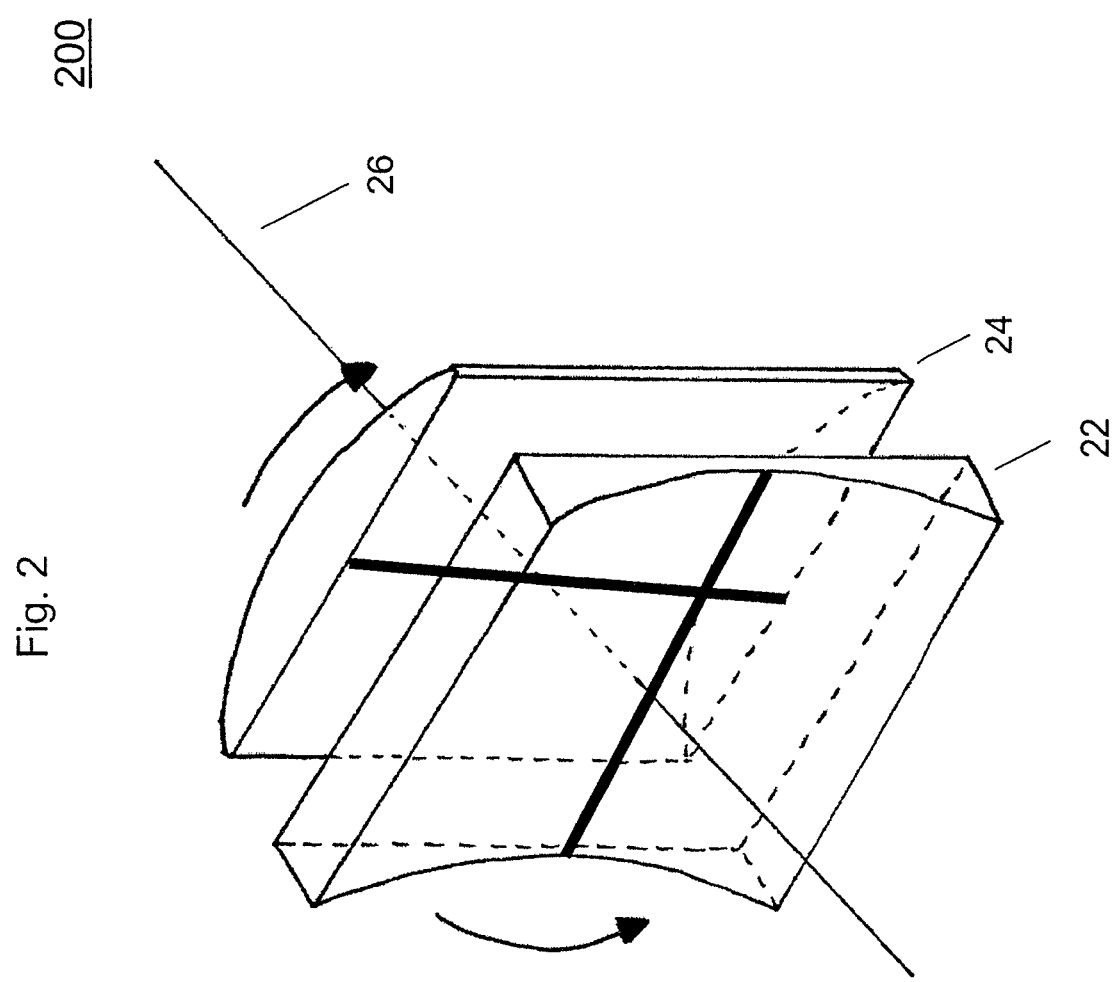
FIG. 2 shows a schematic illustration of a lens system (Stokes lens) which, in accordance with a preferred embodiment of the present invention, can be used for astigmatism compensation in the accommodation stimulation apparatus.

FIG. 2 depicts such a lens system with an adjustable cylindrical power in an exemplary manner. In accordance with the present invention, use is therefore made of a target which has not only a spherical power but additionally an adaptable—in terms of magnitude and direction—cylindrical power.

A conventional target does not appear completely in focus and simultaneously in focus in all directions, particularly for subjects with a high astigmatic component in the refractive error. Depending on the set optical power of the target and the assumed accommodative state, it is either in focus "on average" (when compensating the spherical equivalent) or in e.g. the direction of one of the two principal meridians when compensating the power in the respective principal meridian. If the virtual distance in this case lies in a region in which corresponding accommodative states can be perceived in focus with both principal meridians, there can also be jumping between these two accommodative states, i.e. the eye can assume different accommodative states during the measurement, or in successive measurements, in the case of the same virtual distance, leading to different and therefore imprecise values of the ophthalmological data to be determined (objectively).

As a result of the use according to the invention of an optical system (e.g. of lenses) with cylindrical power of a virtual target, an astigmatic refractive error of the at least one eye of the subject can at least be partly compensated for. An image or virtual target which the subject can perceive completely in focus (apart from the higher-order aberrations which are negligible in this context) is placed in front of him. As a result, both the fixation and accommodation are simplified for him compared to a non-compensated astigmatism of the at least one eye 13 of the subject. Consequently, refraction measurements on the basis of a virtual target can be performed more accurately and reliably since what is decisive in such measurements is that the subject also in fact accommodates to the target. This is not always ensured without corresponding compensation, particularly in the case of subjects with a high astigmatic refractive error, possibly leading to errors in the determination of the refraction.

Moreover, the invention can in many cases significantly reduce signs of fatigue of the eye, which may occur in the case of a conventional (objective) determination of the refraction due to a possibly unsatisfactory accommodation success. As a result, the present invention also promotes faster accommodation of the eye, which enables the faster performance of individual measurements and therefore—if desired—the performance of a plurality of measurements, possibly at different virtual distances (accommodative states), preferably without even increasing the overall measurement time. This also can in turn increase the measurement accuracy.

The preferred device for determining ophthalmological data, as shown in FIG. 1, furthermore has a measuring apparatus, by means of which the ophthalmological data can be measured or registered. The measuring apparatus can preferably correspond to that of a conventional automated refractor or aberrometer. In accordance with the preferred embodiment depicted in FIG. 1, the measuring apparatus substantially comprises a laser 16, a second beam splitter 14 (partly transmissive mirror) and a detector 18. A spherical wave is induced in the eye 13 with the aid of a spatially restricted, in particular focused laser beam, which is emitted by the laser 16 and deflected into the eye 13 by the second beam splitter 14, which spherical wave emanates from the illuminated point on the retina and is refracted in the eye (in particular at the interfaces) and at the surface thereof. Depending on the optical properties of the eye, the light leaves the eye with wavefronts which may deviate to a greater or lesser extent from a spherical form. These wavefronts propagate through the two beam splitters 12 and 14 and are finally detected by the detector 18. For the purposes of determining the refraction, ophthalmological data such as sphere, astigmatism and, particularly in the case of an aberrometer, higher-order aberrations of the examined eye can be established or registered from the detected signal of the wavefront emitted by the eye. Furthermore, further ophthalmological data, such as e.g. the pupil size or, if use is made of a Shack-Hartmann sensor, the wavefront, can also be measured.

FIG. 2 shows a schematic illustration of a lens system which, in addition to a spherical power, also has an adjustable astigmatic power. The lens system (also known as a Stokes lens) consists of two plane cylinders with equal and opposite optical powers (negative plane cylinder 22 and positive plane cylinder 24) which are mounted in a frame (not depicted here) in a manner rotatable against one another about a common optical axis 26. If the two cylinder axes (depicted by thick black lines in FIG. 2) are parallel to one another, the powers of the two cylinders compensate one another and the two together act, at least approximately, like a plane-parallel plate. However, if the axes are perpendicular to one another (as sketched in FIG. 2), this generates a spherocylindrical combination. Here, the spherical power emerges from the power of the individual cylinder. The so-called "astigmatic difference" emerges from the sum of the magnitudes of the inverse radii of curvature of the individual cylinders. Different intermediate values of the astigmatic difference can be set as a result of continuously rotating the cylinder axes.

Figure 3:
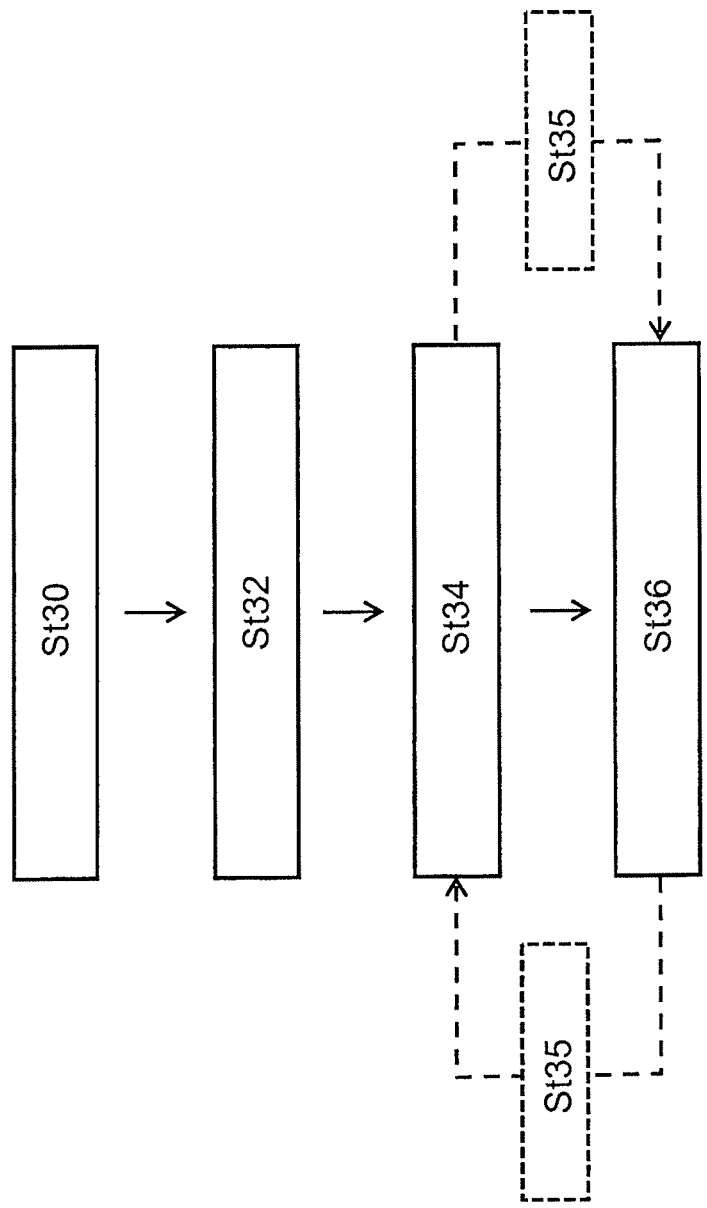
FIG. 3 shows a schematic illustration of a sequence of a method in accordance with a preferred embodiment of the present invention.

FIG. 3 schematically depicts a sequence of a method for determining ophthalmological data, in particular for determining the refraction, in accordance with a preferred embodiment of the present invention. Preferably, the method comprises at least two measurements, a first measurement (pre-measurement) and at least one second measurement (main measurement). Here, in general, a measurement is understood to mean the registration of ophthalmological data.

In order to perform a first measurement, i.e. a pre-measurement, a virtual target with spherical and adjustable astigmatic power is initially projected into the at least one eye of the subject in a first step St30. Since no information about the refractive error of the subject may be available at this time, the virtual target is preferably set to a virtual position which causes a hazy state. The cylindrical power of the virtual target is preferably set to be neutral, i.e. to zero.

In a next step St32 of the described preferred embodiment, a pre-measurement is performed for approximately determining the refractive error, in particular the astigmatic refractive error, of the at least one eye 13 of the subject. Thus, this step St32 preferably contains a registration of a first value of an astigmatic refractive error of the at least one eye of the subject in a first measurement (pre-measurement). Further ophthalmological data, such as e.g. the sphere, can preferably also be measured during this pre-measurement. In the pre-measurement, the same set of ophthalmological data is particularly preferably registered as in the main measurement.

The cylindrical power of the virtual target is set in a subsequent step St34 of the described preferred embodiment to a value which substantially compensates the registered first value of the astigmatic refractive error of the at least one eye of the subject. What this achieves is that the subject can perceive the virtual target substantially without astigmatic errors and consequently perceive it substantially uniformly in focus in all directions.

What is therefore achieved in the subsequent main measurement St36, which can preferably initially likewise be performed in the hazy state, is that the subject perceives the virtual target uniformly out of focus in all directions and does not identify any structures. This is substantially more comfortable for the subject and at the same time ensures good stability of the accommodation in the hazy state. In particular, sphere and/or astigmatism of the at least one eye of the subject are registered with the main measurement. However, additionally, any other items of ophthalmological data can also be registered with the main measurement. If the value for the astigmatism established from the main measurement has changed compared to the pre-measurement, steps St34 and St36 can be repeated immediately for further improvement in the determination of the refraction.

After step St34, the position (i.e. the virtual distance) of the virtual target can be changed in an optional step St35 (depicted with dashed lines in FIG. 3) prior to performing the main measurement. Therefore, it is possible to perform the main measurement not in the hazy state but at a specific accommodation, stimulated by the virtual target, of the eye 13 to be measured. By way of example, it is possible to perform a measurement in the far accommodative state (far measurement) or a measurement in the near accommodative state (near measurement). What is ensured with high probability as a result of setting the astigmatic power, undertaken in step St34, on the basis of the pre-measurement is that the subject also in fact fixes on, or accommodates to, the virtual target during the main measurement. This makes the measurement more reliable and accurate.

After the main measurement was performed with step St36, the position of the virtual target can subsequently be changed (step St35) in order to perform at least one further main measurement for another accommodative state of the eye 13. The virtual distance of the virtual target is preferably successively (i.e. monotonically) reduced between the individual main measurements. The adjustable cylindrical power of the virtual target is preferably set prior to each main measurement by step St35 to a value which substantially compensates the value of the astigmatic refractive error of the at least one eye of the subject registered during the preceding measurement. What this achieves is that the astigmatic refractive error of the subject is substantially compensated for each main measurement and consequently this improves the result of determining the refraction.

LIST OF REFERENCE SIGNS

10 Accommodation stimulation apparatus
12 First beam splitter
13 Eye
14 Second beam splitter
16 Laser/laser diode
18 Detector
22 Negative plane cylinder
24 Positive plane cylinder
26 Optical axis
100 Device for determining ophthalmological data
200 Lens system/Stokes lens as astigmatism compensator
St30 Projecting a virtual target with spherical and adjustable astigmatic power into the at least one eye of the subject
St32 Pre-measurement (first measurement)
St34 Setting the astigmatic power of the virtual target
St35 Changing the virtual position of the virtual target (optional)
St36 Main measurement (second, third, fourth, etc. measurement)

The invention claimed is:

1. A device for determining a set of ophthalmological data of at least one eye of a subject, comprising:
an accommodation stimulation apparatus configured to:
perform a pre-measurement by initially projecting a virtual target with a first spherical power and with an adjustable cylindrical power into the at least one eye of the subject by means of a lens or a lens system that images an object; and
perform a main measurement by changing a spherical power of the virtual target from the first spherical power to a second spherical power by changing the spherical power of the lens or the lens system or by changing the relative position between the lens or the lens system and the object to be imaged, so as to reduce the virtual distance of the virtual target towards a near accommodation limit of the at least one eye, at which the accommodation of the eye can no longer follow the further reduction in the virtual distance, while the virtual target with a cylindrical power is projected into the at least one eye of the subject in such a way that the cylindrical power of the virtual target at least partly compensates a registered first value of the astigmatic refractive error of the at least one eye; and
an optical data measurement device including an illuminator and a detector, the optical data measurement device configured to (i) register ophthalmological data of the at least one eye of the subject, (ii) select, from among each of a number of repeated pre-measurements and main measurements, a measurement at which a maximum accommodation power of the at least one eye of the subject was reached, and (iii) use data obtained via the selected measurement as a result of a near measurement to measure at least one of wavefront, pupil dimensions, and aberrations of higher and lower order.

2. The device as claimed in claim 1, wherein the accommodation stimulation apparatus has at least one lens with a spherical power and at least one lens with a cylindrical power.

3. The device as claimed in claim 1, wherein the accommodation stimulation apparatus comprises a magazine with a multiplicity of cylindrical lenses, each lens having different cylindrical powers such that individual cylindrical lenses and/or a combination of a plurality of cylindrical lenses of the magazine is configurable to project the virtual target.

4. The device as claimed in claim 1, wherein the accommodation stimulation apparatus has an Alvarez lens system.

5. The device as claimed in claim 1, wherein the accommodation stimulation apparatus comprises two lenses which are rotatable in relation to one another and which respectively have at least one cylindrical component in the powers.

6. The device as claimed in claim 5, wherein the accommodation stimulation apparatus has two cylindrical lenses with mutually engaging, mutually facing rotationally symmetric surfaces, plane surfaces.

7. The device as claimed in claim 6, wherein the accommodation stimulation apparatus has a positive and a negative cylindrical lens with equal and opposite powers, said cylindrical lenses being rotatably mounted in relation to one another and preferably being displaceable in relation to one another.

8. The device as claimed in claim 1, wherein the device is embodied as an aberrometer and/or as an automated refractor.

9. The device as claimed in claim 1, wherein the optical data measurement device is configured to register an astigmatic refraction of the at least one eye of the subject, and wherein the cylindrical power of the virtual target is set such that the registered astigmatic refraction of the at least one eye is at least partly compensated.

10. The device as claimed in claim 1, wherein the measuring apparatus is configured to register the ophthalmological data including the first value of the astigmatic refractive error of the at least one eye of the subject.

11. The device as claimed in claim 1, wherein the accommodation stimulation apparatus is further configured to repeatedly change the spherical power of the virtual target at least twice to iteratively adjust the first spherical power to successively reduce the virtual distance of the virtual target towards the near accommodation limit of the at least one eye after each registration of the ophthalmological data of the at least one eye by the optical data measurement device.

12. A method for determining a set of ophthalmological data of at least one eye of a subject, comprising:
registering, by means of a measuring apparatus, a first value of an astigmatic refraction of the at least one eye of the subject;
perform a pre-measurement by initially projecting, by means of an accommodation stimulation apparatus, a virtual target with a first spherical power and with a first cylindrical power into the at least one eye of the subject by means of a lens or a lens system that images an object in such a way that the first cylindrical power of the virtual target at least partly compensates the registered first value of the astigmatic refractive error of the at least one eye;
perform a main measurement by:
changing the spherical power of the virtual target from the first spherical power to a second spherical power by changing the spherical power of the lens or the lens system or by changing the relative position between the lens or the lens system and the object to be imaged, so as to reduce the virtual distance of the virtual target towards a near accommodation limit of the at least one eye, at which the accommodation of the eye can no longer follow the further reduction in the virtual distance, while the virtual target with a cylindrical power is projected into the at least one eye of the subject in such a way that the cylindrical power of the virtual target at least partly compensates the registered first value of the astigmatic refractive error of the at least one eye; and
registering the ophthalmological data of the at least one eye by the measuring apparatus while the eye is stimulated by the accommodation stimulation apparatus to accommodate to the virtual target;
selecting, from among each of a number of repeated pre-measurements and main measurements, a measurement at which a maximum accommodation power of the at least one eye of the subject was reached; and
using data obtained via the selected measurement as a result of a near measurement to measure at least one of wavefront, pupil dimensions, and aberrations of higher and lower order.

13. The method as claimed in claim 12, wherein the registration of the ophthalmological data of the at least one eye of the subject is implemented during a near accommodation of the at least one eye of the subject.

14. The method as claimed in claim 12, wherein the registration of the ophthalmological data comprises a registration of a second value of the astigmatic refractive error of the at least one eye of the subject, and wherein the method further comprises:
projecting the virtual target with a second spherical power and a second cylindrical power into the at least one eye of the subject in such a way that the second cylindrical power of the virtual target at least partly compensates the registered second value of the astigmatic refractive error of the at least one eye; and
registering further ophthalmological data of the at least one eye of the subject.

15. The method as claimed in claim 12, wherein the virtual target simulates a greater virtual object distance in the case of the first spherical power than in the case of the second spherical power.

16. A device for determining a set of ophthalmological data of at least one eye of a subject, comprising:
an accommodation stimulation apparatus configured to project a virtual target with a spherical power and with an adjustable cylindrical power into the at least one eye of the subject by means of a lens or a lens system that images an object; and
an optical data measurement device including an illuminator and a detector, the optical data measurement device configured to register ophthalmological data of the at least one eye of the subject;
wherein the optical data measurement device is configured to perform a pre-measurement comprising:
initially projecting, by means of the accommodation stimulation apparatus, a virtual target with a first spherical power into the at least one eye of the subject; and
registering, by means of the optical data measurement device, a first value of an astigmatic refractive error of the at least one eye of the subject associated with the first spherical power; and
wherein the optical data measurement device is further configured to perform a main measurement comprising:
projecting, by means of the accommodation stimulation apparatus, a virtual target with a second spherical power into the at least one eye of the subject to thereby reduce the virtual distance of the virtual target towards a near accommodation limit of the at least one eye, at which the accommodation of the eye can no longer follow the further reduction in the virtual distance, in such a way that the cylindrical power of the virtual target at least partly compensates the registered first value of the astigmatic refractive error of the at least one eye; and
registering, by means of the optical data measurement device, ophthalmological data including a second value of the astigmatic refractive error of the at least one eye of the subject;
wherein the optical data measurement device is further configured to select, from among each of a number of repeated pre-measurements and main measurements, a measurement at which a maximum accommodation power of the at least one eye of the subject was reached, and to use data obtained via the selected measurement as a result of a near measurement to measure at least one of wavefront, pupil dimensions, and aberrations of higher and lower order.

17. A method for determining a set of ophthalmological data of at least one eye of a subject, comprising performing a pre-measurement and a main measurement,
wherein the pre-measurement comprises:
projecting a virtual target with a first spherical power and with an adjustable cylindrical power into the at least one eye of the subject by means of a lens or a lens system that images an object, and
registering a first value of an astigmatic refraction error of the at least one eye of the subject associated with the first spherical power; and wherein the main measurement comprises:
  initially projecting a virtual target with a second spherical power into the at least one eye of the subject to thereby reduce the virtual distance of the virtual target towards a near accommodation limit of the at least one eye, at which the accommodation of the eye can no longer follow the further reduction in the virtual distance, by means of a lens or a lens system that images an object in such a way that the cylindrical power of the virtual target at least partly compensates the registered first value of the astigmatic refractive error of the at least one eye, and
  registering the ophthalmological data including a second value of the astigmatic refractive error of the at least one eye while the eye is stimulated by the accommodation stimulation apparatus to accommodate to the virtual target;
selecting, from among each of a number of repeated pre-measurements and main measurements, a measurement at which a maximum accommodation power of the at least one eye of the subject was reached; and
using data obtained via the selected measurement as a result of a near measurement to measure at least one of wavefront, pupil dimensions, and aberrations of higher and lower order.

* * * * *